US005688906A

United States Patent [19]
Jen et al.

[11] Patent Number: 5,688,906
[45] Date of Patent: Nov. 18, 1997

[54] HIGHLY EFFICIENT NONLINEAR OPTICAL POLYIMIDES

[75] Inventors: Kwan-Yue Alex Jen, Old Bridge; Kevin Joel Drost, Spotswood, both of N.J.

[73] Assignee: Enichem S.p.A., Italy

[21] Appl. No.: 500,384

[22] Filed: Aug. 7, 1995

Related U.S. Application Data

[63] Continuation of Ser. No. 132,707, Oct. 6, 1993, abandoned, which is a continuation-in-part of Ser. No. 101,368, Aug. 2, 1993, Pat. No. 5,514,799, which is a continuation-in-part of Ser. No. 158,184, Nov. 24, 1995, which is a continuation of Ser. No. 626,358, Dec. 12, 1990, abandoned.

[51] Int. Cl.$^6$ .......................... C08G 69/26; C08G 73/10
[52] U.S. Cl. .................. 528/353; 528/68; 528/72; 528/75; 528/287; 528/289; 528/291; 528/292; 528/306; 528/337; 528/345; 528/347; 528/350; 528/363; 528/403; 528/422; 526/258; 526/288; 526/289; 526/298; 526/299; 526/306; 526/311; 526/312; 526/328
[58] Field of Search ...................... 528/310, 289, 528/287, 292, 306, 350, 403, 353, 337, 345, 347, 363, 422, 68, 72, 75; 526/258, 288, 289, 298, 299, 311, 312, 306, 328

[56] References Cited

U.S. PATENT DOCUMENTS

| | | | |
|---|---|---|---|
| 4,719,281 | 1/1988 | Choe | 528/310 |
| 4,783,151 | 11/1988 | Choe | 528/310 |
| 4,892,681 | 1/1990 | Miyata et al. | 252/582 |
| 4,894,186 | 1/1990 | Gordon et al. | 252/582 |
| 4,894,263 | 1/1990 | Dubois et al. | 428/1 |
| 4,933,112 | 6/1990 | DeMartino et al. | 252/582 |
| 4,935,292 | 6/1990 | Marks et al. | 428/220 |
| 5,156,774 | 10/1992 | Leising et al. | 252/582 |
| 5,189,134 | 2/1993 | Mignami et al. | 528/403 |
| 5,272,218 | 12/1993 | Cheng et al. | 526/258 |

FOREIGN PATENT DOCUMENTS

| | | |
|---|---|---|
| 0493716 | 7/1992 | European Pat. Off. |
| 2255336 | 11/1992 | United Kingdom. |
| 2267095 | 11/1993 | United Kingdom. |
| WO9009616 | 8/1990 | WIPO. |
| WO 91/03001 | 3/1991 | WIPO. |

OTHER PUBLICATIONS

Rossi, "Polyimides" *Engineered Materials Handbook, vol. 3: Adhesives and Sealants*, 151–62 (ASM International, Materials Park, Ohio, 1991) copyright.

Nicoud et al., Ch. II–III *Nonlinear Optical Properties of Organic Molecules and Crystals, vol. I*, (Chemla and Zyss, Eds., Academic Press, Inc., New York 1987) 227–96.

*Primary Examiner*—Jeffrey C. Mullis
*Assistant Examiner*—P. Hampton-Hightower
*Attorney, Agent, or Firm*—Lerner, David, Littenberg, Krumholz & Mentlik

[57] ABSTRACT

A method for forming a polyamic acid having nonlinear optical (NLO) or pre-NLO side chains, which method includes the steps of:

(1) providing a bis-(aromatic dicarboxylic acid anhydride) containing at least one NLO or pre-NLO side chain having the structure represented by:

D-R-A wherein D, R and A form a delocalized resonance configuration in which R is a pi-conjugated non-centrosymmetric moiety, A is hydrogen or an electron withdrawing moiety and D is an electron donating moiety covalently linked to the bis-(aromatic dicarboxylic acid anhydride); and (2) reacting the bis-(aromatic dicarboxylic acid anhydride) with an aromatic diamine to form a polyamic acid having NLO or pre-NLO side chains. Methods for preparing polyamic acids having NLO or pre-NLO side chains by reacting aromatic diamines having NLO or pre-NLO side chains with bis-(aromatic dicarboxylic acid anhydrides) are also disclosed. Methods of forming the polyamic acids into polyimides having NLO side chains are also included.

47 Claims, No Drawings

HIGHLY EFFICIENT NONLINEAR OPTICAL POLYIMIDES

This is a continuation of application Ser. No. 08/132,707, filed on Oct. 6, 1993, which has been abandoned, and which, in turn, is a Continuation-In-Part of U.S. patent application Ser. No. 08/101,368, filed Aug. 2, 1993 U.S. Pat. No. 5,514,799. The present Application is also a Continuation-In-Part of U.S. patent application Ser. No. 08/158,184, filed Nov. 24, 1993, which is a Continuation of U.S. patent application Ser. No. 07/626,358, filed Dec. 12, 1990, which has been abandoned.

BACKGROUND OF THE INVENTION

1. Field of the Invention

The present invention relates to polyamic acids and polyimides prepared therefrom having nonlinear optical (NLO) properties. In particular, the present invention relates to polyamic acids and polyimides prepared therefrom with NLO side chains covalently attached thereto, thereby improving the chemical and thermal stability of the NLO moiety.

The NLO side-chains of the polymers of the present invention are stable in processing solvents and at processing temperatures used in the production of electro-optic devices. When suitably oriented, the compounds are capable of highly efficient second harmonic generation and electro-optic modulation of an electromagnetic wave having a wavelength between 300 nm and 2,000 nm. The present invention further relates to methods for preparing the polymer compositions of the present invention, as well as intermediate compounds useful in the preparation of the inventive polymers.

2. Description of the Prior Art

Highly efficient NLO materials capable of doubling or tripling the frequency of incident life are currently of great scientific and technological interest for use in optical telecommunications, signal processing and the construction of optical computers. Nonlinear optics is concerned with the interaction of electromagnetic fields in various media to produce new fields which may be altered in phase, frequency or amplitude. The NLO effective material upon an electromagnetic field is a function of the second and higher order terms of the following equation:

$$P = \alpha E + \beta E^2 + \gamma E^3 + \ldots$$

P is the polarization of material, E is the intensity of the electric field, and the coefficients $\alpha$, $\beta$ and $\gamma$, etc., are indicative of the NLO susceptibility of the material. Such coefficients are constant for a given material but vary from material to material. The second order coefficient, $\beta$, for a given material, is indicative of the second harmonic generation properties of the material, with second harmonic generation efficiencies increasing as the value of $\beta$ increases.

Candidate NLO materials should possess good physical properties, such as high optical transparencies, low dielectric constants and high laser damage thresholds. The material should also possess the molecular nonlinearity required of NLO materials, and particularly, high $\beta$ values, fast response times and nonlinear susceptibility over a broad range of wavelengths, particularly of wavelengths between about 300 nm and 2,000 nm.

Recent efforts in the development of NLO materials have focused upon non-centrosymmetric organic materials with large delocalized pi-electron systems, which exhibit great nonlinear susceptibilities and can be varied to optimize the desired physical and mechanical properties. This includes the single benzene ring derivative disclosed by U.S. Pat. No. 4,894,186 to Gordon and the compounds derived from two to four benzene rings separated by pi-electron conjugated carbon-carbon, carbon-nitrogen and nitrogen-nitrogen bridges disclosed by U.S. Pat. No. 4,892,681 to Myata et al., U.S. Pat. No. 4,894,263 to Dubois et al., U.S. Pat. No. 4,933,112 to DeMartino et al. and U.S. Pat. No. 4,935,292 to Marks et al, and the five-membered heteroaromatic ring compounds linked by pi-electron conjugated bridges disclosed by U.S. patent application Ser. No. 07/626,358 filed Dec. 12, 1990. The disclosure of this patent application is hereby incorporated herein by reference thereto.

To induce charge asymmetry, and consequently second order nonlinear polarizability, an aromatic ring at one end of the NLO compound structure is substituted with an electron donating group, while on the other end of the NLO compound structure, an aromatic ring is substituted with an electron accepting group. The dipole of the compound structure can then be aligned in accordance with the method described by U.S. Pat. No. 4,935,292, the disclosure of which is hereby incorporated herein by reference thereto.

However, pi-electron conjugated bridges linking the aromatic or heteroaromatic rings of NLO compounds are a source of thermal and photochemical instability. This is addressed by copending and commonly owned U.S. patent application Ser. No. 07/930,732 filed Aug. 14, 1992, the disclosure of which is hereby incorporated herein by reference thereto. This application discloses NLO compounds derived from highly conjugated fused ring structures of two or three aromatic or heteroaromatic rings, at least one of which is a five-membered heteroaromatic ring. The pi-electron conjugated bridges are eliminated. This application also discloses NLO compounds derived from one to four non-fused five-membered heteroaromatic rings linked together without pi-conjugated bridges.

The stability of non-centrosymmetric organic materials with large delocalized pi-electron systems in processing solvents and host polymers at processing temperatures is an important parameter in their application in electro-optic devices. Because high-$T_g$ polyimide based electro-optic polymers are likely candidates to be used in the production of NLO devices, candidate NLO materials must survive the stringent processing conditions required to produce stable electro-optic polyimides.

Most polyimides are coated as an amic acid prepolymer, which, after solvent removal, is thermally converted in a ring-closing reaction to the final polyimide. During this imidization process, the very acidic environment (pH=2), polar processing solvents and by-products formed at high temperatures (150°–200° C.) are very reactive to the NLO compounds. Thus far, molecules that have been inherently stable to approximately 300° C. have not been completely stable in polyamic acids while being cured to polyimides. Many decompose near the $T_g$ of the polymers. This is believed to be caused either by the residual polar solvents which complex with amic acid, or by the reactive products formed during the high temperature imidization process.

The difficulties of formulating polyamic acids containing NLO compounds capable of being cured to form polyimides strongly hinders the rapid development of highly efficient NLO polymers. Until now, high temperature NLO polyimides have been limited to guest/host-type materials in which the NLO compound is dissolved into a polyamic acid or polyimide matrix. While this represents a convenient means of formulation, there are several severe deficiencies.

NLO compounds cannot be dissolved in polyamic acids and polyimides at acceptable loading levels because of the poor solubility of the NLO) compounds in the processing solvents and the polymer matrices. This is attributable, in part, to the low compatibility of the NLO compound for the polymer matrix, which results in sublimation or, alternatively, aggregation of the NLO compound. The NLO compound aggregates scatter light, resulting in high optical loss. In addition, the incompatibility of the NLO compounds for the polymers gives rise to a plasticization of the polymers, lowering the $T_g$ of the polymer matrix-NLO compound combination.

NLO compounds that are stable in polyamic acid solvents, both at room temperature and at curing temperatures, are not well established in the literature. Accordingly, a need exists for NLO compounds that are stable under polyimide curing and processing conditions.

SUMMARY OF THE INVENTION

This need is met by the present invention. It has now been discovered that polyimides with NLO side chains covalently attached thereto can be prepared by covalently bonding NLO or pre-NLO compounds to polyamic acids and then curing the resulting polymer. The resulting compounds demonstrate both thermal and chemical stability during the thermally induced intramolecular condensation of the polyamic acids to polyimides. Pre-NLO side chains can be functionalized to NLO side chains following the imidization of the polyamic acid.

Therefore, in accordance with the present invention, there is provided a method for forming a polyamic acid having NLO or pre-NLO side chains, which method includes the steps of:

(1) providing a bis-(aromatic dicarboxylic acid anhydride) containing at least one NLO or pre-NLO side chain having the structure represented by Formula I:

  (I)

wherein D, R and A form a delocalized resonance configuration in which R is a pi-conjugated non-centrosymmetric moiety, A is hydrogen or an electron withdrawing moiety and D is an electron donating moiety covalently linked to the bis-(aromatic dicarboxylic acid anhydride); and (2) reacting the bis-(aromatic dicarboxylic acid anhydride) with an aromatic diamine to form a polyamic acid having NLO or pre-NLO side chains.

R can be any pi-conjugated non-centrosymmetric organic moiety exhibiting optical nonlinearity. R may contain from one to ten aromatic or heteroaromatic rings or fused ring systems, linked together so as to form a delocalized resonance configuration. Suitable linkages include pi-electron conjugated carbon-carbon, carbon-nitrogen and nitrogen-nitrogen bridges. At least one five- or six-membered heteroaromatic ring is preferably present, alone, or as part of the fused ring system, which heteroaromatic ring contains at lest one heteroatom selected from O, N, S, Se or Te. The number or size of the fused ring systems should not be so large as to interfere with the solubility of the NLO compounds in processing solvents.

One aspect of this method of the present invention preferably forms the bis-(aromatic dicarboxylic acid anhydrides) containing at least one NLO or pre-NLO side chain by linking together two aromatic dicarboxylic acid anhydrides with an NLO or pre-NLO compound. Therefore, according to preferred embodiments of this method of the present invention, the step of providing a bis-(aromatic dicarboxylic acid anhydride) includes the step of reacting two moles of an aromatic dicarboxylic acid anhydride substituted with a moiety capable of undergoing nucleophilic substitution with one mole of an NLO or pre-NLO compound having the structure of Formula I, in which R and A are the same as described above with respect to Formula I and D represents an electron donating moiety containing two nucleophilic substituents, so that a bis-(aromatic dicarboxylic acid anhydride) is obtained having an NLO or pre-NLO side chain.

Polyamic acids having NLO or pre-NLO side chains can also be prepared by reacting bis-(aromatic dicarboxylic acid anhydrides) with aromatic diamines containing at least one NLO or pre-NLO side chain. Therefore, in accordance with the present invention, there is provided a method for forming a polyamic acid having NLO or pre-NLO side chains, which method includes the steps of:

(1) providing an aromatic diamine containing at least one NLO or pre-NLO side chain having the structure represented by Formula I, in which R and A are the same as described above with respect to Formula I and D is an electron donating moiety, covalently linked to the aromatic diamine; and (2) reacting the aromatic diamine with a bis-(aromatic dicarboxylic acid anhydride) to form a polyamic acid having NLO or pre-NLO side chains.

One aspect of this method of the present invention preferably forms the aromatic diamine containing at least one NLO or pre-NLO side chain by reacting an aromatic amine with an NLO or pre-NLO compound. Therefore, according to preferred embodiments of this method of the present invention, the step of providing an aromatic diamine includes the step of reacting two moles of an aromatic amine substituted with a moiety capable of undergoing nucleophilic substitution with one mole of an NLO or pre-NLO compound having a structure corresponding to Formula I, in which R and A are the same as described above with respect to Formula I and D represents an electron donating moiety containing two nucleophilic substituents, so that an aromatic diamine is obtained having an NLO or pre-NLO side chain.

Alternatively, to obtain an aromatic diamine having a single aromatic ring and at least one NLO or pre-NLO side chain, the step of providing an aromatic diamine includes the step of reacting one mole of an aromatic amine substituted with a moiety capable of undergoing nucleophilic substitution with one mole of an NLO or pre-NLO compound having the structure of Formula I, in which R and A are the same as described above with respect to Formula I and D represents an electron donating moiety containing two alkylamine substituents, so that an aromatic diamine is obtained having an NLO or pre-NLO side chain.

The polyamic acid derived from either method is then cyclized to a polyimide by a thermally induced intramolecular condensation. Therefore, methods in accordance with this aspect of this embodiment of the present invention may further include the step of heating the polyamic acid so that the polymer is cyclized to form a polyimide having NLO or pre-NLO side chains.

Pre-NLO side chains are utilized when the desired electron withdrawing moiety is sensitive to the conditions of polyamic acid imidization. Pre-NLO side chains are defined as NLO side chains having no electron accepting groups, that is, side chains in which A is hydrogen. Once the polyamic acid is imidized, the resulting polyimide can be reacted to attach electron accepting groups to the pre-NLO side chains to provide a polymeric NLO material. Therefore, when A is hydrogen, methods in accordance with the present invention may further include the step of covalently attaching at least one electron accepting group to the polyimide side chain.

The NLO and pre-NLO polyamic acid compounds produced by the methods of the present invention are uniquely stable under imidization conditions in solvents such as N-methyl-pyrrolidone (NMP), dimethylacetamide (DMAC), dimethylformamide (DMF), and the like, and are stable in polyimides up to 300° C. The NLO and pre-NLO side chain substituted polyamic acids are thus useful intermediates in the preparation of NLO side chain substituted polyimides.

Therefore, in accordance with the present invention, NLO and pre-NLO side chain substituted polyamic acids are provided. In accordance with this embodiment of the present invention, polyamic acids are provided, formed by the methods of the present invention and substituted with an NLO or pre-NLO side chain having the structure of Formula I in which R and A are the same as described above with respect to Formula I and D is an electron donating moiety covalently linked to the polyamic acid.

The NLO and pre-NLO side chain substituted polyamic acids of the present invention may then be cyclized by thermally induced intramolecular condensation to form NLO and pre-NLO side chain substituted polyimides. Therefore, yet another embodiment of the present invention provides polyimides formed by the thermally induced intramolecular condensation of the polyamic acids of the present invention, and substituted with NLO or pre-NLO side chains having the structure of Formula I, wherein R and A are the same as described above with respect to Formula I and D is an electron donating moiety covalently linked to the polyimide.

The NLO side chain substituted polyamic acids and polyimides of the present invention possess heretofore unobtained chemical and thermal stability, without sacrificing second order nonlinearity. In addition to possessing good second order NLO susceptibilities and thermal and chemical stability, the incorporation of NLO compounds into polyimides as covalently attached side chains greatly enhances the loading level of the NLO compounds in the polymer system and eliminates phase separation. This decreases the optical attenuation for channel wave guides.

The enhanced loading level, as well as the liquid-crystalline orientation effect obtained by covalent attachment of the side chains provides enhanced electro-optic coefficients compared to the inclusion of guest NLO compounds in a host polyimide matrix. Furthermore, the covalent attachment of the NLO compounds on the polymer chain provides better alignment stability for the electro-optic signal.

Another advantage from using polyamic acids and polyimides is the wide variety of glass-transition temperatures that may be attained by modification of the structure of the diamine with which the bis-acid anhydride is copolymerized. This approach provides almost unlimited variations of polymers to fine tune the structural and electrical properties of the NLO compounds. Finally, the NLO compounds of the present invention are soluble in spin-casting solvents, have high laser damage thresholds, are easily synthesized and have well-known and understood chemical properties.

DETAILED DESCRIPTION OF THE PREFERRED EMBODIMENT

The NLO side chain substituted polyimides prepared by the process of the present invention, once suitably oriented, exhibit a high second order NLO susceptibility. The polyimides of the present invention are formed by the reaction of an aromatic diamine with a bis-(aromatic dicarboxylic acid anhydride) to form a polyamic acid, which then undergoes a ring-closing reaction to form the polyimide structure. The cyclization to the polyimide is accomplished by a thermally induced intramolecular condensation. This is performed at elevated temperatures around 200°–300° C. in solvents like NMP, DMAC and DMF. The covalent attachment of the NLO compounds to the polyimide provides thermal and chemical stability under these conditions.

The NLO and pre-NLO side chains have a structure represented by Formula I in which D, R and A form a delocalized resonance configuration, in which D is an electron withdrawing moiety covalently linked to the polyimide or polyamic acid, A is hydrogen or an electron withdrawing moiety, and R is a pi-conjugated non-centrosymmetric organic moiety. R can be any pi-conjugated non-centrosymmetric organic moiety exhibiting optical nonlinearity. Suitable non-centrosymmetric organic moieties contain from one to ten aromatic rings or fused ring systems. Two or more rings or fused ring systems are linked together to form a delocalized resonance configuration. Within the present specification, "heteroaromatic" rings are defined as being limited to aromatic heterocyclic rings, thereby excluding carbocyclic rings such as phenyl groups. "Aromatic" rings are defined as generically including carbocyclic and heterocyclic rings. The heteroaromatic rings of the present invention contain one or more heteroatoms selected from O, N, S, Se and Te.

The non-centrosymmetric organic moieties of the present invention preferably contain from one to four aromatic rings or fused ring systems. The aromatic rings or fused ring systems within each non-centrosymmetric organic moiety may be the same or different.

For non-centrosymmetric organic moieties containing multiple rings or fused ring systems, it is preferable that at least one ring alone, or within a fused ring system, be a five-membered heteroaromatic ring having one heteroatom selected from O, N, S, Se and Te. The heteroaromatic rings may optionally include up to three additional N atoms. Preferably, the five-membered heteroaromatic rings possess a structure corresponding to Formula II:

in which Y is C or N and X is selected from O, N, S, Se and Te.

Preferably, the non-centrosymmetric organic moieties containing multiple rings or fused ring systems contain two or more of the five-membered heteroaromatic rings, alone, or as part of a fused ring system. Most preferably, all of the rings and organic moieties containing multiple rings or fused ring systems are five-membered heteroaromatic rings, and all fused ring systems contain a five-membered heteroaromatic ring. When two or more heteroaromatic rings are present in a non-centrosymmetric organic moiety, the rings may have the same or different heteroatoms.

The fused ring systems should not be so large as to hinder the solubility of the NLO compounds in processing solvents. The point at which fused ring system size interferes with solubility is easily identified by those of ordinary skill in the art. Fused ring systems of two to three rings are preferred, and two ring systems are most preferred.

For non-centrosymmetric organic moieties containing multiple rings or fused ring systems, adjacent rings or fused ring systems may be linked by from one to three pi-electron conjugated functional groups such as carbon-carbon, carbon-nitrogen or nitrogen-nitrogen functional groups. Preferably, the adjacent rings or fused ring systems are bridged by one or two of the conjugated functional groups. When adjacent rings or fused ring systems are bridged by two or three functional groups, the conjugated functional groups may be the same or different than the conjugated functional groups between adjacent rings or fused ring systems and may vary within an NLO side chain. When the ring is heteroaromatic, or the fused ring system contains a heteroaromatic ring, the linkage is preferably substituted on the ring alpha to a heteroatom. For six-membered rings, alone, or within fused ring systems, the linkage is substituted para to another linkage, an electron donating group, or an electron acceptor group.

The use of pi-electron conjugated functional groups to bridge adjacent rings or fused ring systems in NLO compounds is essentially conventional to the art of NLO active organic materials. Examples of suitable ring- or fused ring system-bridging functional groups known in the art include, but are not limited to, —CH=CH—, —N=N—, —CH=N—, —CH=N—N=CH—, —C≡C—, and (CH=CH)$_j$—, with j being from one to three.

The adjacent rings or fused ring systems of non-centrosymmetric organic moieties of linked aromatic rings or fused ring systems may also be linked by non-conjugated linkages. The adjacent rings or fused ring systems may also be covalently bonded between single ring members to directly link the rings or fused ring systems without forming a fused structure of the adjacent rings or fused ring systems.

The pi-conjugated non-centrosymmetric organic moieties of the present invention can also include a single aromatic ring or fused ring system. The preferred single ring is a five-membered heteroaromatic ring as defined above. Fused rings are preferred over single rings, and fused ring systems containing at least one five-membered heteroaromatic ring, as defined above are preferred fused ring systems.

Regardless of whether the non-centrosymmetric organic moiety contains single or multiple rings or fused ring systems, the fused ring systems suitable for use in the present invention contain two or three rings. The two- or three-ring fused ring systems can consist entirely of five-membered heteroaromatic rings. A fused ring system consisting of three five-membered heteroaromatic rings is preferred over a system consisting of two five-membered heteroaromatic rings.

The configuration of multiple heteroaromatic rings within a fused ring system is not critical, and may be an all "up" configuration or an alternating "up" and "down" configuration, as depicted in the above-cited U.S. patent application Ser. No. 07/930,732. The two or three five-membered heteroaromatic rings may have the same or different heteroatoms.

The fused ring systems of the present invention are not limited to structures containing five-membered heteroaromatic rings. Fused ring systems containing benzene rings, pyridine rings, and the like, and combinations thereof are also suitable for use with the present invention. When a two- or three-ring system includes pyridine, the pyridine should not be quaternized. Such ionic species cause severe current leakage during the dipole-alignment electric field poling process.

The fused ring compounds of the present invention are limited to two- and three-ring fused ring systems so as not to hinder the solubility of the NLO compounds in processing solvents. Three-ring fused ring systems are preferred because of their greater second order nonlinearity.

From the foregoing description, the aromatic and fused ring systems represented by R as being suitable for use with the present invention can be easily identified by those of ordinary skill in the art. Suitable rings and ring systems include, but are not limited to, pyrrole, furan, thiophene, imidazole, oxazole, thioazole, triazole, tetrazole, pyrazole, pyrimidine, pyridine, purine, quinolines, carbazole, benzene, naphthalene, furazan, pyrazine, indole, isoindole, indazole, phenothiazine, benzotriazole, anthracene, phenanthrene, azophenanthrenes, quinazolines, pteridine, pyrones, chromones, and the like.

To induce charge asymmetry, the non-centrosymmetric organic moiety is substituted with an electron donating group and an electron accepting or withdrawing group. As noted above, the electron accepting or withdrawing group may be attached to the NLO side chain subsequent to cyclization of the polyamic acid to a polyimide. Prior to attachment of the electron accepting group, the side chain is referred to as a pre-NLO side chain. Thus, A in Formula I represents hydrogen for pre-NLO side chains and an electron accepting group for NLO side chains. The electron donating group is depicted as D in Formula I.

Electron donating and electron accepting groups are preferably substituted on five-membered heterocyclic rings that are either single rings or members of fused ring systems, although this is not essential. When substituted on heteroaromatic rings, the electron donating group or electron accepting group is preferably substituted alpha to a heteroatom. For non-centrosymmetric organic moieties containing multiple rings or fused ring systems, the electron donating and electron accepting groups are preferably attached to aromatic or heteroaromatic rings or fused ring systems at opposite ends of the multiple ring structure. For non-centrosymmetric organic moieties consisting of a single fused ring system, the electron donating and accepting groups are substituted to ring members of different rings.

The electron donating groups and electron accepting groups are substituted to the non-centrosymmetric organic moiety so as to form a delocalized resonance configuration. Positions for substituting electron donating and electron accepting groups to form delocalized resonance configurations can be readily determined by those of ordinary skill in the art. Examples of typical delocalized resonance configurations are depicted in the above-cited U.S. patent application Ser. No. 930,732.

The electron donating and accepting groups that are capable of inducing charge asymmetry to non-centrosymmetric organic moieties are essentially conventional to the art of NLO active organic materials. Any functional group capable of withdrawing electrons from a fused ring system is suitable for use as an electron accepting group. Examples of suitable electron accepting groups known in the art include —NO$_2$, —CN, —CHO, —COR$_3$, —COOR$_3$, —PO(OR$_3$)$_2$, —SO$_2$R$_3$, —SO$_3$R$_3$, —PO(R$_3$)$_2$, dicyanovinylpyrones and —CX=CYZ, wherein X, Y and Z are independently selected from hydrogen, —CN, —NO$_2$, —COR$_3$, —COOR$_3$, —SO$_2$R$_3$, —PO(R$_3$)$_2$ and —PO(OR$_3$)$_2$. R$_3$ is an alkyl group containing up to 15 carbon atoms, and preferably is a methyl group. Other suitable electron accepting groups include N,N-dialkylbarbituric acids, N,N-dialkylthiobarbituric acids, N,N-diarylbarbituric acid, N,N-diarylthiobarbituric acid, rhodamines, hydrantoins, oxazolines, and a ring system having a structure corresponding to Formula III:

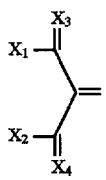
(III)

wherein $X_1$ and $X_2$ form a saturated or unsaturated five- to eight-membered cyclic ring or two-ring system having five- to eight-membered rings, and $X_3$ and $X_4$ are independently selected from O, S and $CI_1I_2$, wherein $I_1$ and $I_2$ are independently selected from —CN, —NO$_2$, —COR$_3$, —COOR$_3$, —SO$_2$R$_3$, —PO(R$_3$)$_2$, —PO(OR$_3$)$_2$. Again, R$_3$ is an alkyl group containing up to 15 carbon atoms, and preferably is a methyl group. Examples of ring structures defined by the structure of Formula III include 3-dicyanovinylindane-1-sulfone, 1,3-bis-sulfonylindane, indane-1,3-dione, 3-dicyanovinylindane-1-one and 1,3-bisdicyanovinylindane.

Strong electron accepting groups are preferred, examples of which include —C(CN)=C(CN)$_2$, —NO$_2$, dicyanoethylene, dinitroethylene, cyanonitroethylene, nitroesterethylene, N,N-dialkylbarbituric acids, N,N-dialkylthiobarbituric acids and the group having the structure depicted in Formula IV, wherein $X_1$, $X_2$, $X_3$ and $X_4$ and $I_1$ and $I_2$ are the same as described above with respect to the structure. The most preferred strong electron accepting group is —C(CN)=C(CN)$_2$, a tricyanoethylene or tricyanovinyl group. Guidance for the selection of electron withdrawing moieties can be found in Nicoud et al., Ch. II–III of *Nonlinear Optical Properties of Organic Molecules and Crystals*, Vol. 1 (Chemla and Zyss, Eds., Academic Press, Inc., New York 1987), p.233.

Essentially any functional group capable of releasing electrons into the pi-electron system of an aromatic or heteroaromatic ring or fused ring system is suitable for use as an electron donating group, provided that the group is also capable of being covalently attached to the polyamic acid or polyimide. Otherwise, electron donating groups that are used to induce charge asymmetry to the structure of Formula I are also essentially conventional to the art of NLO active organic materials. Guidance for the selection of electron donating groups can also be found in Nicoud et al.

Examples of suitable electron donating groups known in the art include —NR$_6$R$_7$—, —OR$_8$—, —SR$_8$—, —TeR$_8$—, —SeR$_8$—, CH=NR$_9$—, —CH=N—NR$_6$R$_7$— and —CH=C[N(R$_6$R$_7$)]$_2$—, wherein R$_6$ and R$_7$ are independently selected from hydrogen, alkyl groups containing up to 12 carbon atoms and groups derived from functionalized alkyl groups containing up to 12 carbon atoms through which the electron donating group is covalently linked to the polyamic acid or polyimide. The alkyl groups are functionalized with nucleophilic substituents, examples of which include alkoxy, aminoalkyl, alkylhalide, hydroxyalkyl, alkylsulfide, alkylisocyanate, alkylisothiocyanate, alkylthiol, alkylazide, alkylcarboxylic, alkylsulfonic, alkylalkene and alkylalkyne groups. At least one of R$_6$ and R$_7$ is an alkyl group derived from a functionalized alkyl group through which the electron donating group is covalently linked to the polymer.

R$_6$ and R$_7$ may also together form a cyclic group containing up to eight carbon atoms, including groups such as pyrrolidine, piperidine, piperazine and morpholine, provided that the cyclic group is substituted with at least one alkyl group derived from a functionalized alkyl group through which the electron donating group is covalently linked to the polymer. The functionalized alkyl groups are the same as described above with respect to the non-cyclic R$_6$ and R$_7$ moieties.

R$_8$ is a group derived from a functionalized alkyl group containing up to six carbon atoms and R$_9$ is a group derived from a functionalized alkyl group containing up to ten carbon atoms, through either of which electron donating group is covalently linked to the polymer. Again, the functionalized alkyl groups are the same as described above with respect to R$_6$ and R$_7$.

Another example of suitable electron donating groups is depicted by the structure of Formula IV:

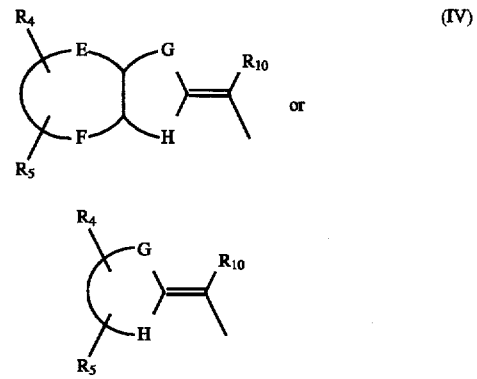
(IV)

wherein E, F, G and H are members of a saturated or unsaturated five- to eight-membered cyclic ring or two-ring system having five- to eight-membered rings that are electron donating in nature. E, F, G and H are —CH—, —CH$_2$—, or heteroatoms independently selected from O, N, S, Se, Te and —NR$_{11}$—. R$_4$, R$_5$, R$_{10}$ and R$_{11}$ are independently selected from hydrogen, alkyl groups containing up to 18 carbon atoms and alkyl groups derived from functionalized alkyl groups containing up to 18 carbon atoms through which the electron donating group is covalently linked to the polyamic acid or polyimide. At least one of R$_4$, R$_5$, R$_{10}$ and R$_{11}$ is a group derived from a functionalized alkyl group through which the electron donating group is covalently linked to the polymer. The functionalized alkyl groups are the same as described above with respect to R$_6$ and R$_7$.

Examples of suitable one- or two-ring electron donating groups include dithiane and dithiolium groups such as 1,3-dithiolium, 2-benzo-1,3-dithiolium and 2-ethylenedithio-1,3-dithiolium, and the like. Whether or not a ring is electron donating in nature to meet the definition of membership in the groups is understood by those of ordinary skill in the art.

Strong electron donating groups are preferred, which significantly increase the second order NLO properties of the compound of the invention. Examples of strong electron donating groups are —NR$_6$R$_7$, and groups such as pyrrolidine, dithiane, piperidine, piperazine, morpholine and the above dithiolium groups, substituted with a group derived from a functionalized alkyl group through which the electron donating group is covalently linked to the polyimide acid or polyimide. The most preferred strong electron donating group is a 2-ethylenedithio-1,3-dithiolium group covalently linked to the polyamic acid or polyimide through a functionalized alkyl group derivative.

The aromatic or heteroaromatic rings or fused ring systems of the NLO compounds of the present invention may optionally be further substituted. Any number of functional groups can be substituted on the aromatic or heteroaromatic ring or rings, provided that the groups are not so large or so numerous to cause undesirable steric hindrance effects, the occurrence of which will be clear to those of ordinary skill in the art.

The preferred embodiment of the present invention includes a second electron donating group, or a second electron accepting group, or both, attached to the same rings, or ring members of fused rings systems, as the respective first electron donating group and the first electron accepting group described above, so that all of the electron donating and electron accepting groups present, together with the non-centrosymmetric organic moiety, form a delocalized resonance configuration. The second electron donating or accepting group may be the same or different than the corresponding first electron donating or accepting group. The second electron donating group may or may not function to covalently link the NLO side chain to the polymer. The inclusion of a second electron donating or electron accepting group increases the second order NLO properties of the resulting material as compared to materials having single-substitution of electron donating and electron accepting groups.

The non-centrosymmetric organic moieties upon which the NLO compounds of the present invention are based are prepared by well-known methods widely reported in the prior art. The preparation of many of these moieties is disclosed in the above-cited U.S. patent application Ser. Nos. 66,358 and 930,732. Some of the non-centrosymmetric organic moieties are commercially available. The electron accepting groups and electron donating groups can be substituted to the non-centrosymmetric organic moiety using conventional methods.

As noted above, the polyamic acids of the present invention having NLO and pre-NLO side chains are formed by the reaction of either an aromatic diamine with a bis-(aromatic dicarboxylic acid anhydride) containing at least one NLO or pre-NLO side chain, or by the reaction of a bis-(aromatic dicarboxylic acid anhydride) with an aromatic diamine containing at least one NLO or pre-NLO side chain.

The aromatic dicarboxylic acid anhydrides from which the bis-(acid anhydrides) of the present invention are derived include phthalic anhydride, trimellitic anhydride, naphthalene anhydride, and the like. Examples of bis-(aromatic dicarboxylic acid anhydrides) include:

3,3',4,4'-benzopheninetetracarboxylic dianhydride pyromellitic dianhydride
3,3',4,4'biphenyltetracarboxylic dianhydride
(3,4-dicarboxyphenyl)hexafluropropane dianhydride
4,4'-oxydiphthalic anhydride
3,3',4,4'-diphenylsulfonetetracarboxylic dianhydride
5-(2,5-dioxotetrahydrol)-3-methyl-3-cyclohexane-1,2-dicarboxylic anhydride,
ethylene glycol bis(anhydrio-trimellitate)

Aromatic diamines suitable for use in the preparation of polyamic acids from which polyimides may be derived are well-known to those of ordinary skill in the art. As previously noted, the aromatic diamine may be selected to fine-tune the $T_g$ of the polymer. For example, aromatic diamines providing polyimides with a more rigid structure include:

2,4-toluene diamine
p-phenyldiamine
2,2-bis(3-amino-4-methylphenyl)-hexafluoropropane
2,2'-bis(4-aminophenyl)hexafluropropane
3,3'-dihydroxy-4,4'-diaminobiphenyl
3,3'-dimethyl-4,4'-diaminobiphenyl
2,5-diaminobenzotrifluoride
1,4-bis(4-aminophenoxyl)benzene
1,3-bis(4-aminophenoxyl)biphenyl
4,4'-oxydianiline
3,4'-oxydianiline
3,3'-diaminodiphenylsulfone
4,4'-diaminodiphenylsulfone
9,10-bis(4-aminophenyl)anthracene
O-tolidine sulfone
9,9-bis(4-aminophenyl)fluorene
4,4'-diaminodiphenyl sulfide Aromatic diamines that provide polyimides with a softer, less rigid, more amorphous structure include Bioaniline P, Bisaniline M, bis-(4-[4-aminophenoxy]phenyl)ether, tetramethylphenylmethylene diamine, diethylmethylene diamine, and the like.

The bis-(aromatic dicarboxylic acid anhydrides) from which the polyamic acids of the present invention are derived may have ring-substituted NLO or pre-NLO side chains. Ring substitution of the bis-(aromatic dicarboxylic acid anhydride) is obtained by using a bis-(aromatic dicarboxylic acid anhydride) in which an aromatic ring of either or both aromatic dicarboxylic acid anhydride is substituted with a moiety capable of undergoing nucleophilic substitution. Such moieties are relatively identified by those of ordinary skill in the art, with a preferred moiety being acid chlorides.

The bis-(aromatic dicarboxylic acid anhydride) is then reacted with an NLO compound having a structure represented by Formula I in which R and A are the same as described above with respect to Formula I and D is an electron donating group functionalized with a nucleophilic substituent. The means by which the bis-(aromatic dicarboxylic acid anhydrides) may be ring-substituted with the above-described NLO and pre-NLO compounds are well-known and essentially conventional to those of ordinary skill in the art.

Thus, D may be one of the above-described electron donating groups in which $R_6$ or $R_7$ includes an alkyl group functionalized with a nucleophilic substituent and containing up to 12 carbon atoms, $R_8$ is a functionalized alkyl group containing up to 6 carbon atoms, $R_9$ is a functionalized alkyl group containing up to 10 carbon atoms, or at least one of $R_4$, $R_5$, $R_{10}$ and $R_{11}$ of the structure of Formula IV is a functionalized alkyl group containing up to 18 carbon atoms.

The NLO or pre-NLO side chains of the bis-(aromatic dicarboxylic acid anhydrides) need not be ring-substituted. Side chain substitution at a position other than an aromatic ring is obtained by using a bis-(aromatic dicarboxylic acid anhydride) having a non-aromatic moiety, which is substituted with a moiety capable of undergoing nucleophilic substitution. The bis-(acid anhydride) is then reacted with the above-described NLO compound having an electron donating group functionalized with a nucleophilic substituent. Again, the means by which the bis-(acid anhydrides) may be side-chain substituted with the above-described NLO and pre-NLO compounds are well-known and essentially conventional to those of ordinary skill in the art.

Preferably, the bis-(aromatic dicarboxylic acid anhydrides) are prepared by linking together two aromatic dicarboxylic acid anhydrides with an NLO or pre-NLO compound. Examples of suitable aromatic dicarboxylic acid anhydride starting materials include phthalic anhydride, trimellitic anhydride, 1,8-naphthalic anhydride, and the like, which are substituted with a moiety capable of undergoing nucleophilic substitution. The acid anhydrides are reacted with an NLO or pre-NLO compound having the structure of Formula I, in which the electron donating moiety contains two nucleophilic substituents. A bis-(aromatic dicarboxylic acid anhydride) is obtained having an NLO or pre-NLO side chain.

Accordingly, D may be one of the above-described electron donating groups that are functionalized with two nucleophilic substituents, such as —$NR_6R_7$, —CH=N—$NR_6R_7$ and —CH=C[$N(R_6R_7)$]$_2$. For the above-described electron donating groups, $R_6$ and $R_7$ may also together form one of the listed cyclic groups containing up to 8 carbon atoms, provided that the cyclic group is functionalized with two nucleophilic substituents. D may also represent that the structure of Formula IV in which at least two of $R_4$, $R_5$, $R_{10}$ and $R_{11}$ contain nucleophilic substituents.

The reaction is performed at a temperature between about −10° and about 25° C. in an aprotic solvent. Examples of suitable aprotic solvents include halogenated hydrocarbons such as methylene chloride, chloroform, chlorobenzene, and the like. The NLO or pre-NLO side chain substituted bis-(aromatic dicarboxylic acid anhydride) is then worked up by conventional methods involving extraction with water, drying and solvent washing, with a 1:1 ratio of methylene chloride and hexane being preferred.

The NLO or pre-NLO side chain substituted aromatic diamines may be similarly prepared. That is, ring-substituted aromatic diamines are prepared from aromatic diamines that are ring-substituted with moieties capable of undergoing nucleophilic substitution, and aromatic diamines having non-aromatic moieties that are substituted with moieties capable of undergoing nucleophilic substitution. Either compound is then reacted with the compound having the structure of Formula I in which the electron donating group is functionalized with a nucleophilic substituent. Again, the means by which the aromatic diamine may be substituted with the above-described NLO and pre-NLO compounds are well-known and essentially conventional to those of ordinary skill in the art.

Preferably, the aromatic diamines are formed by reacting aromatic amines with an NLO or pre-NLO compound. Examples of suitable aromatic amine starting materials include, aniline, 2-, 3- or 4-aminophenol, and the like, which are substituted with a moiety capable of undergoing nucleophilic substitution and reacted with an NLO or pre-NLO compound having an electron donating group containing two leaving groups, so that an aromatic diamine is obtained having an NLO or pre-NLO side chain.

Two moles of the aromatic amine may be reacted with one mole of the NLO or pre-NLO compound, to form an aromatic diamine in which two aromatic amines are linked by an NLO or pre-NLO side chain. D of the NLO or pre-NLO compound of Formula I is again one of the above-described electron donating groups containing two nucleophilic substituents.

Aromatic diamines having an NLO or pre-NLO side chain may also be prepared by reacting one mole of an aromatic amine substituted with a moiety capable of undergoing nucleophilic substitution with one mole of an NLO or pre-NLO compound having an electron donating moiety containing two amine substituents. One of the amines functions to attach the NLO or pre-NLO compound as a side chain to the aromatic amine, while the other amine functions as the second amine of the diamine.

The aromatic amines and NLO) or pre-NLO compounds are reacted in a polar solvent, such as DMF, DMSO, NMP, at a temperature ranging between about 0° and about 50° C. The NLO or pre-NLO side chain substituted aromatic diamine is then worked up by conventional methods involving extraction with dichloromethane, drying, evaporating and solvent washing, with an ice-cooled alcohol being preferred.

The bis-(aromatic dicarboxylic acid anhydride) and the aromatic diamine are then copolymerized in a 1:1 ratio to form the polyamic acid of the present invention. Either the bis-(acid anhydride), the aromatic diamine, or both, may contain an NLO or pre-NLO side chain. Both bis-(acid anhydrides) and aromatic diamines having no NLO or pre-NLO side chains may be included in the reaction mixture.

Thus, it will be appreciated that the polyamic acids of the present invention need not be completely substituted with NLO groups. The present invention includes polymers having ratios of NLO substituted monomeric subunits to unsubstituted monomeric subunits between about 1:99 and about 75:25. Substitution ratios between about 10:90 and about 70:30 are preferred. Substitution ratios less than about 60:40 are more preferred in order that the polymer remains soluble in processing solvents. The most preferred substitution ratio is about 50:50.

The polymerization of the polyamic acid of the present invention is essentially conventional and is readily understood by those of ordinary skill in the art. The polymerization is performed in a common solvent for the reagents, typically a higher boiling point polar solvent such as NMP, DMAC, DMSO and the like. Higher boiling point solvents are selected because of the elevated temperatures required for cyclization of the polyamic acid.

The cyclization of the polyamic acid to the polyimide is accomplished by a thermally induced intramolecular condensation at a temperature between about 120° C. to about 200° C. Typically, this ring-closing reaction is performed by directly refluxing the reaction mixture in which the polyamic acid was polymerized. Higher boiling point solvents which form azeotropes with water, such as dichlorobenzene, xylenes and trichlorobenzenes are preferably used because the cyclization reaction generates water, which may then be removed as a solvent azeotrope.

Once the reaction is complete, the polyimide having NLO or pre-NLO side chains is precipitated with a lower alkyl alcohol, such as methanol or isopropanol, filtered and dried under vacuum. The polymer can then be further purified by conventional methods, typically by repeated dissolution and reprecipitation from the lower alkyl alcohol.

As mentioned above, pre-NLO side chains are utilized when the desired electron withdrawing moiety is sensitive to the conditions of polyamic acid imidization. Pre-NLO side chains were defined as NLO side chains in which A is hydrogen, because the side chains have no electron accepting group. Electron accepting groups that are sensitive to the conditions of polyamic acid imidization include tricyanovinyl, dicyanovinyl, thiobarbituric acid, barbituric acid, 1,3-dicyanovinylindane and cyanonitrovinyl electron accepting groups.

Following polyamic acid imidization, the resulting polyimide with pre-NLO side chains can be reacted to attach electron accepting groups to the side chains to provide a polymeric NLO material. Alternatively, prior to attachment of electron accepting groups, the chain length of the pre-NLO side chain can be extended to increase the NLO activity of the polymer by the attachment of additional pi-conjugated non-centrosymmetric organic moieties contributing to optical nonlinearity. Procedures by which the chain length of NLO chains may be extended are described in the above-cited U.S. patent application Ser. No. 07/626,358.

The method by which a polymer having pre-NLO side chains can be reacted to attach electron accepting groups such as tricyanovinyl groups to provide a polymeric NLO material is essentially conventional and well understood by those of ordinary skill in the art. For example, the polymer having pre-NLO side chains can be reacted with tetracyanoethylene to attach tricyanovinyl electron accepting groups, or an aldehyde-substituted pre-NLO side chain can be reacted with malononitrile, nitroacetonitrile, thiobarbituric acid, etc., to obtain other electron accepting groups. The preferred electron accepting group for subsequent attachment to pre-NLO side chains is the tricyanovinyl group.

Suitable basic solvents for the attachment of electron accepting groups include DMF, DMAC, NMP, pyridine, tertiary amines, and the like. The preferred solvent is DMF. A reaction mixture is prepared by dissolving the polymer with pre-NLO side chains and the reagent from which the electron accepting group will be derived, such as tetracyanoethylene, in one or more of the above solvents. The reaction mixture is heated to a temperature between about 40° C. and about 90° C., and preferably to about 60° C. to attach electron accepting groups to the polyimide having pre-NLO side chains.

Higher temperatures will result in an increased rate of reaction. And even higher rates can be achieved by pressurizing the reaction vessel to elevate the boiling point of the solvent, allowing the reaction to proceed at an even higher temperature. However, a reaction temperature of 60° C. is preferred to minimize inter- and intra-molecular cross reactions.

The degree of electron accepting group attachment is limited only by the number of pendant pre-NLO side chains available for attachment of electron accepting groups. Therefore, a slight equivalent excess of the reagent from which the electron accepting group is derived over the polymer should be used.

The reaction mixture should be maintained at a constant state of mild agitation to ensure uniform mixing. It is also preferred that the reaction mixture be maintained under an atmosphere of an inert gas.

Once the reaction is complete, the polymer may be worked up again as described above by precipitation with a lower alkyl alcohol, followed by filtration and drying under vacuum. Further purification can again be achieved by repeated dissolution and reprecipitation from the lower alkyl alcohol.

Films of the NLO polyimides of the present invention may be formed by spin-coating, after which the films may be repetitively annealed prior to poling at an elevated temperature near the $T_g$ of the material. Following annealing, the dipoles of the side chains may be aligned by application of an intense electric field (0.2–1.0 MV cm$^{-1}$) at temperatures near the $T_g$. The foregoing sequence of spin-coating, annealing and poling is essentially conventional and disclosed in U.S. Pat. No. 4,935,292, the disclosure of which is hereby incorporated herein by reference thereto.

It is disclosed in U.S. Pat. No. 4,932,292 and SPIE Proceeding No. 1147, 74–83 (1989) that further stabilization of the NLO side chain alignment can be achieved by a radiation-induced or chemical-induced cross-linking of the polymer matrix. This process is also essentially conventional, and the disclosure of which in U.S. Pat. No. 4,935,292 is also hereby incorporated herein by reference thereto.

The preferred pre-NLO and NLO polyamic acids and polyimides of the present invention typically have weight-average molecular weights between 2,500 and about 50,000 daltons measured by gel permeation chromatography. The incorporation of electron accepting groups increases the $T_g$'s of the polymer with pre-NLO side chains.

The electro-optic coefficient of an NLO-active poled polymer film is proportional to the product of the molecular second order nonlinear optical susceptibility coefficient β, and the molecular ground state electric dipole moment, μ. The molecular β is dependent upon the frequency at which the measurement is performed because of the resonance effect near the absorption peak. A method to compare molecules with different absorption properties by extrapolation of the β value measured at a specific frequency to zero frequency using a two-level model is disclosed by Singer, J. Opt. Soc. Am., B6, 1339–50 (1989). The β value at the extrapolated frequency is defined $β_0$. The NLO-active molecules of the present invention can exhibit values of the $β_0μ$ product as high as about 9,000 in units of 10$^{-48}$ esu measured at a wavelength of 1,907 nm.

Thus, it can be appreciated that the present invention provides NLO compounds in which the moiety exhibiting nonlinear optical properties has been rendered stable to the conditions of polyimide cyclization and the elevated temperatures at which the annealing and dipole aligning steps for these polymers are typically performed. Such conditions are also encountered when forming electro-optic devices from the NLO polymers of the present invention. These polymers, and the NLO side chains attached thereto, possess the chemical and thermal stability required for these conditions, together with second order nonlinear optical properties and the physical, mechanical and optical properties required of an optical material.

The following examples further illustrate the present invention, and are not to be construed as limiting the scope thereof. Unless otherwise indicated, materials were obtained from Aldrich Chemical Supply. All parts and percentages are by weight unless expressly indicated to be otherwise, and all temperatures are in degrees Celsius.

EXAMPLES

Example 1

Preparation Of A Bis-(Aromatic Dicarboxylic Acid Anhydride) With A Pre-NLO Side Chain

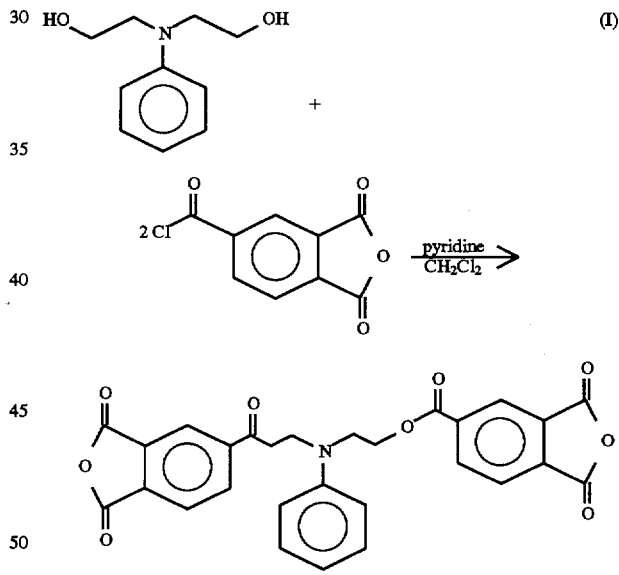

A three-necked flask with condenser and addition funnel was charged with trimellitic anhydride acid chloride (4.21 g, 20.0 mmol), 1.62 mL pyridine (20 mmol) and 60 mL methylene chloride and cooled to 0° C. in an ice bath. N,N-di(2-hydroxyethyl)aniline (1.8124 g, 10 mmol) in 40 mL methylene chloride was added dropwise to this mixture over an addition time of approximately 30 minutes. After addition, the mixture was stirred at 0° C. for another two hours.

The reaction product was worked up by a quick extraction with water, followed by drying (Na$_2$SO$_4$), evaporation and washing with 200 mL of a 1:1 ratio blend of methylene chloride and hexane. The product was then dried to yield 4.7 g of the bis-(aromatic dicarboxylic acid anhydride) with a pre-NLO side chain (89% yield).

Example 2

Preparation Of a Polyimide with a pre-NLO Side Chain

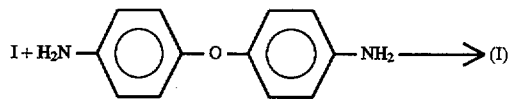

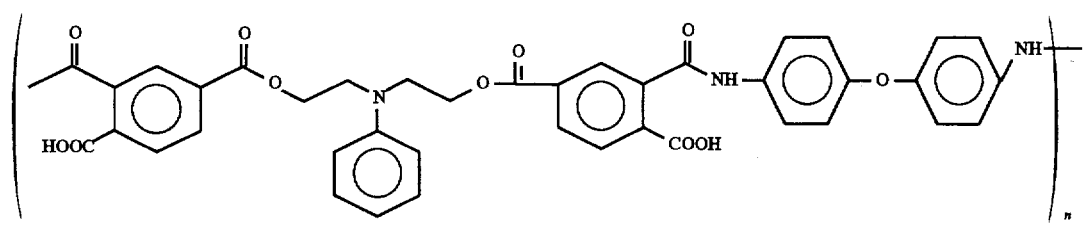

To a stirred solution of the bis-(aromatic dicarboxylic acid anhydride) having a pre-NLO side chain of Example 1 (0.53 g, 1 mmol) in 4 mL of dry NMP under argon at room temperature was added one equivalent of p-aminophenyl ether (0.2 g, 1 mmol). The mixture was stirred at room temperature overnight to form a polyamic acid with pre-NLO side chains.

8 mL of 1,2-dichlorobenzene was added and the mixture was then refluxed for three hours to cyclize the polyamic acid to a polyimide. 400 mL of methanol was added to the resulting solution to precipitate the polyimide having the pre-NLO side chains (0.59 g, 86% yield), which was then worked up as in Example 1.

Example 3

Tricyanovinylation Of The Polyimide Pre-NLO Side Chains

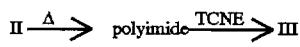

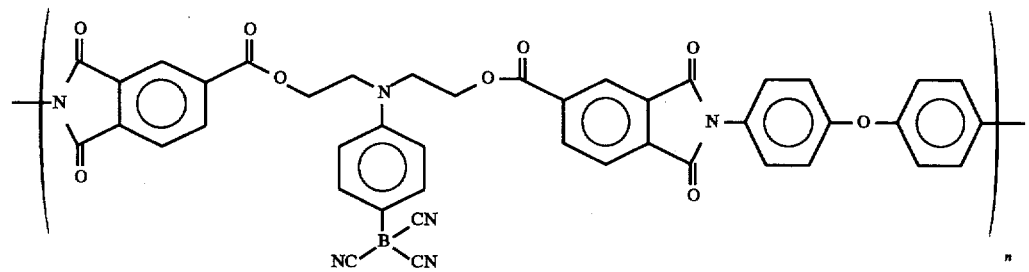

To a stirred solution of the polyimide of Example 2 having pre-NLO side chains (0.2 g) in 0.2 mL DMF was added 0.1 g tetracyanoethylene. The mixture was stirred at 50° C. overnight to tricyanovinylate the pre-NLO side chains of the polymer.

The resulting solution was added dropwise to 400 mL of agitated methanol to precipitate the polymer. The reddish polymer was collected and dried at 80° C. under vacuum for two hours to get 0.21 g of product (91% yield).

The polymer structure was confirmed by proton and carbon-13 NMR differential scanning calorimetry (DSC) and by UV-visible spectrophotometry.

Example 4

Synthesis of 4-Formyl-Diacetyl-N-phenyldiethanolamine

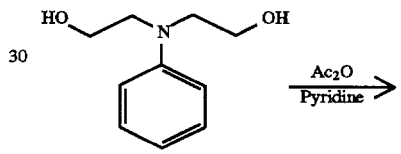

-continued

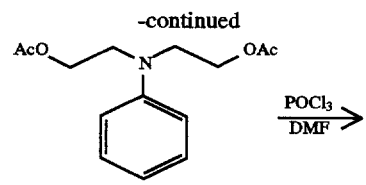

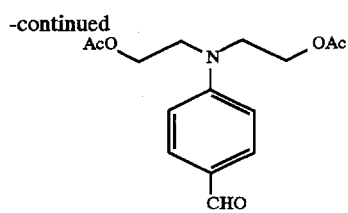

A solution of N-phenyldiethanolamine (25.0 g, 0.138 mol), acetic anhydride (31.0 g, 0.31 mol), and pyridine (25.0 g, 0.356 mol) was heated to reflux for approximately two hours under an argon atmosphere. The resulting solution was cooled and vacuum distilled (160° C., 1 torr) to yield a diacetate (34.3 g, 93.7%) as a pale golden colored oil. Phosphorus oxychloride (22.0 g, 0.144 mol) was added dropwise at 0° C. to 100 mL of N,N'-dimethylformamide (DMF), and the resulting mixture was stirred at 0° C. for two hours. A solution of diacetate (34.32 g., 0.129 mol) in DMF (100 mL) was added slowly, and the reaction mixture was heated to 90° C. for three hours. After cooling, the solution was poured onto 2 L of ice water containing 60 g (5 equiv) of sodium carbonate. The mixture was stirred overnight and the resulting solid was collected by vacuum filtration and used without further purification. The resulting liquid was extracted with dichloromethane (3×250 mL), dried ($Na_2SO_4$), concentrated and distilled (200° C., 0.1 torr) to give additional product which crystallized upon cooling. The two fractions were combined to give a total of 36.1 g, (95% yield from diacetate) as a pale brown solid.

Example 5

Synthesis of (Trans)-7-[4-(1-diacetyldiethanolamino benzene)]ethenyl thiophone

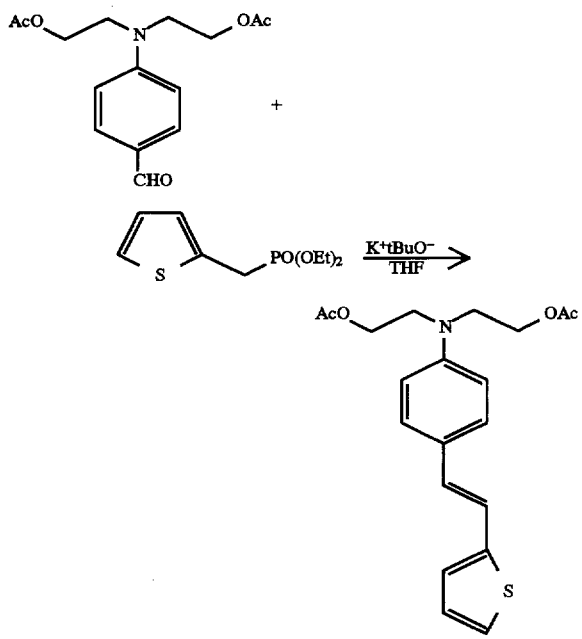

To a stirred solution of the 4-formyldiacetyl-N-phenyldiethanolamine of Example 4, (15.0 g, 51.12 mmol), ethyl thiophene phosphonate ester (15.0 g, 64.02 mmol) and dry, freshly distilled tetrahydrofuran (150 mL) under argon at 0° C. was added potassium t-butoxide (5.71 g., 51.0 mmol). The mixture was stirred in the absence of light overnight with warming to room temperature under argon. The mixture was concentrated in vacuo, and the residue was dissolved in dichloromethane (300 mL), washed with water (3×200 mL), dried ($Na_2SO_4$), and concentrated onto 20 g silica. This silica was added to a medium pressure column packed with silica. The column was eluted with hexane/dichloromethane (5:1) with a gradient to pure dichlomethane to afford the desired stilbene (11.0 g, 75%) as a pale yellow solid.

Example 6

Synthesis of (Trans)-7-[4-(1-diethanolamino benzene)]ethenyl thiophene

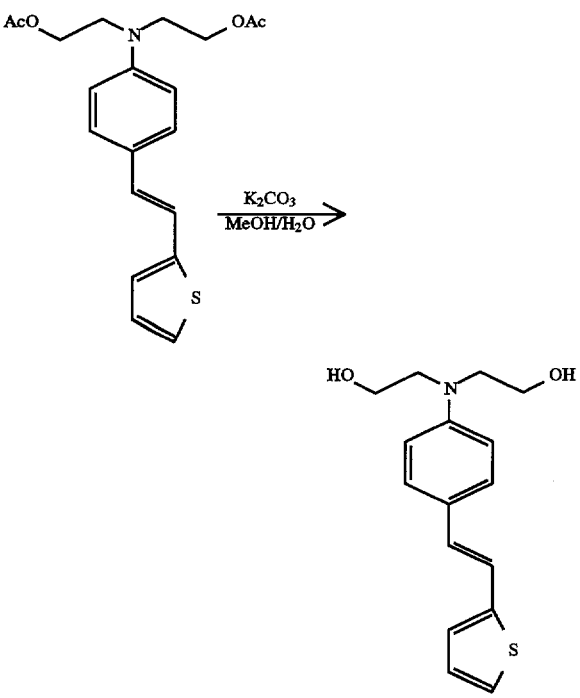

A solution of the diacetyl stilbene (10.0 g, 26.77 mmol) of Example 5 in methanol (1000 mL) and water (100 mL) was treated with potassium carbonate (7.77 g, 56.21 mmol) and warmed to 40° C. overnight. The resulting solution was concentrated in vacuo near dryness. The aqueous material was extracted with dichloromethane (2×200 mL) and washed repeatedly with water (3×100 mL). The combined organic layers were dried ($Na_2SO_4$), concentrated onto silica (15 g) and purified by medium pressure chromatography using a mixture of ethyl acetate/hexane (1:1) with a gradient to pure ethyl acetate to give the desired product (6.7 g, 86%) as a tan solid.

Example 7

Synthesis of (Trans)-7-[4-(1-diethanolamino benzene)]ethenyl-9-dicyanovinyl-11-methyl pyrne

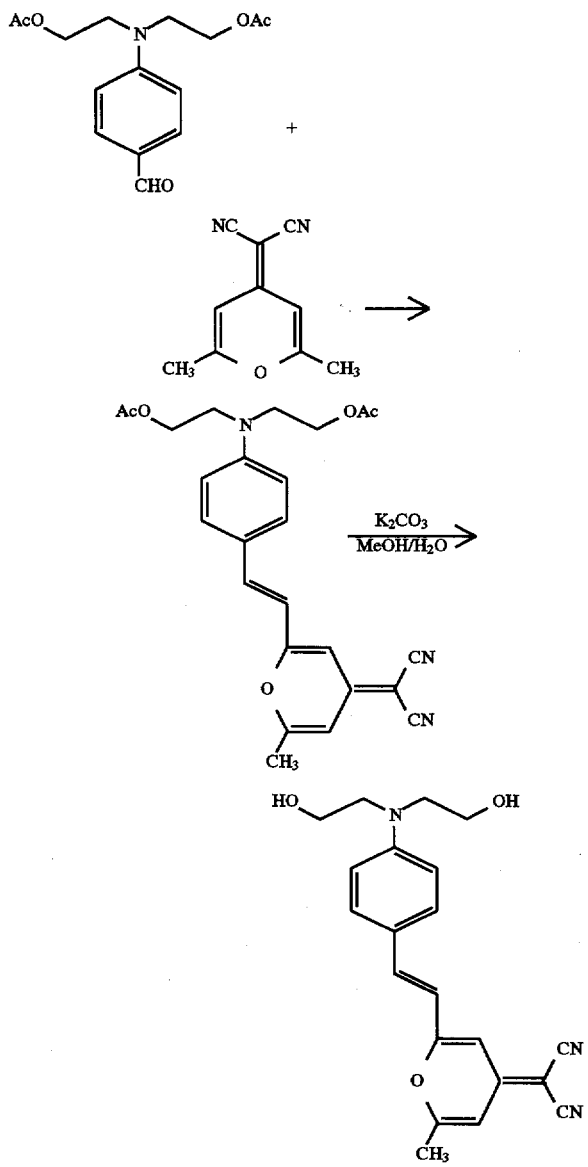

A solution of 2,6-dimethyl-4-dicyanovinyl-γ-pyrone (7.17 g, 41.6 mmol), piperidine (1.05 g, 13.2 mmol), acetic anhydride (0.42 g, 4.11 mmol), and acetic acid (0.42 g, 6.99 mmol) in DMF (60 mL) was heated to 80° C. under an argon atmosphere for two hours. At this time, the 4-formyl-diacetyl-N-phenyldiethanolamine of Example 4 (12.24 g, 41.6 mmol) was added and the mixture was heated for an additional hour at 80° C. The resulting mixture was poured into ice water (300 mL), extracted with dichloromethane (2×200 mL), dried (Na$_2$SO$_4$), and concentrated onto silica (20 g). The mixture was purified by column chromatography using a gradient from 4:1 (Hexane/Ethyl Acetate) to pure ethyl acetate. The diacetate (10.2 g, 55%) was isolated as an orange solid. A solution of the diacetate (8.0 g, 17.9 mmol) in methanol (1.2 L) and water (200 mL) was treated with potassium carbonate (5.0 g, 37.6 mmol) and warmed to 40° C. overnight. The resulting solution was concentrated in vacuo onto silica (15 g) and purified by medium pressure chromatography using a mixture of ethyl acetate/acetone (25:1) with a gradient to ethyl acetate/acetone (10:1) to give the desired product (5.21 g, 86%) as a red solid.

Example 8

Synthesis of N,N'-Bis(2-Aminoethyl) aniline

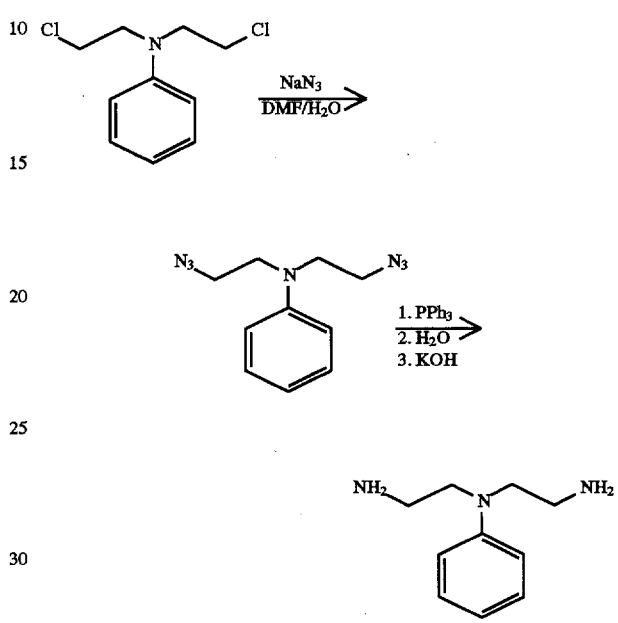

To a solution of N,N'-bis(2-chloroethyl) aniline (10.0 g, 45.85 mmol) in DMF (75 mL) was added sodium azide (5.98 g, 92.2 mmol and the resulting mixture was heated to 100° C. under an argon atmosphere. When the mixture reached this temperature, water was added until the solution became clear (approx. 5 mL). The solution was heated for three hours at this temperature at which time sodium azide was again added (1.1 g, excess), and the mixture was heated for an additional two hours. The resulting solution was cooled, poured into water (500 mL), and extracted with dichloromethane (2×250 mL). The organic layers were combined, dried (Na$_2$SO$_4$), concentrated and purified by column chromatography using pure hexane with a gradient to hexane/dichloromethane (4:1) to yield pure diazide (8.6 g, 81.1%) as an oil that solidified upon cooling in the freezer. To a solution of N,N'-bis(2-azoethyl) aniline (3.92 g, 16.95 mmol) in dry tetrahydrofuran (50 mL) under an argon atmosphere was added triphenyl phosphine (8.95 g, 34.07 mmol). The mixture was stirred at room temperature until all the bubbling had stopped (approximately 3–4 hours). To this solution was then added water (10 mL) and the mixture was stirred overnight. Potassium hydroxide pellets were added to make the solution basic and the mixture was stirred for an additional two hours. The resulting mixture was concentrated and mixed with water (200 mL). The solution was acidified with HCL (concentrated), extracted with dichloromethane (2×200 mL) to remove any neutrals, rebasified with potassium hydroxide and extracted with dichloromethane (2×200 mL). The organic layers were combined, dried (Na$_2$SO$_4$), and concentrated to yield pure diamine (2.46 g, 81.2% from diazide).

Example 9

Synthesis of Pre-NLO Polyimide

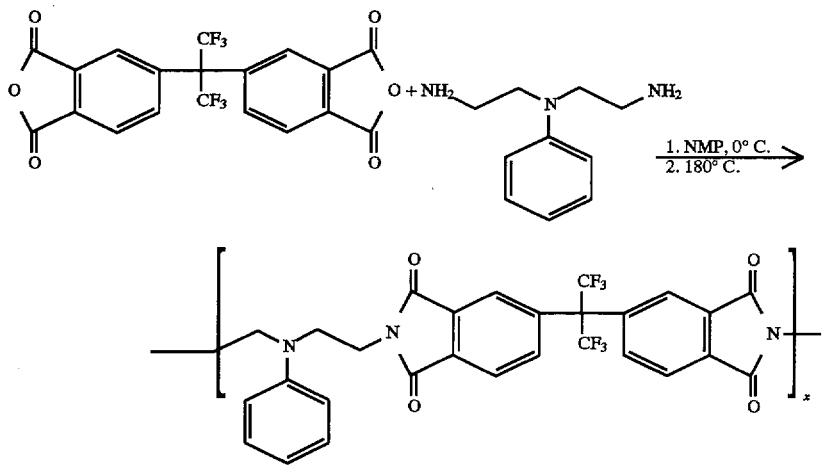

To a solution of the N,N'-bis(2-aminoethyl) aniline of Example 8 (5 g, 27.89 mmol) in N-methylpyrolidinone (100 mL, NMP) at 0° C. was added 2,2'-bis(3,4-dicarboxyphenyl) hexafluoropropane dianhydride (12.38 g, 27.89 mmol) and the solution was allowed to warm to room temperature overnight. The resulting solution was then heated to 180° C. under an argon atmosphere for 3–4 hours. The resulting solution was cooled and added dropwise to an agitated solution of methanol (500 mL) to precipitate the polymer. The resulting precipitate was collected and purified by being redissolved into NMP (100 mL) and reprecipitated with methanol. The resulting imide (16.0 g, 94%) was dried at (60° C., 1 torr).

Example 10

Cyanation of Pre-NLO Polyimide

Tetracyanoethylene (3.2 g, 25.0 mmol) was added to an ice cooled stirred solution of the imide of Example 9 (10.0 g, 16.5 mmol) in dimethylformamide (100 mL) under argon. The reaction mixture was allowed to warm up to room temperature and then heated to 100° C. for two hours. The resulting solution was cooled and added dropwise to an agitated solution of methanol (500 mL) to precipitate the polymer. The resulting red solid was vacuum filtered and redissolved in DMF (74 mL) and reprecipitated with methanol (500 mL). The desired red polymer (12.5 g, 95%) was dried at 60° C. (1 torr.)

The NLO side chains of the polymers of the present invention thus possess a combination of NLO properties and thermal and chemical stability heretofore unobtained with polyimides. At the same time, the compounds have good solubility in processing solvents, high laser damage thresholds, are easily synthesized and have well-known and understood chemical properties. The wide variety of NLO side chains that can be attached to the polyimides creates a

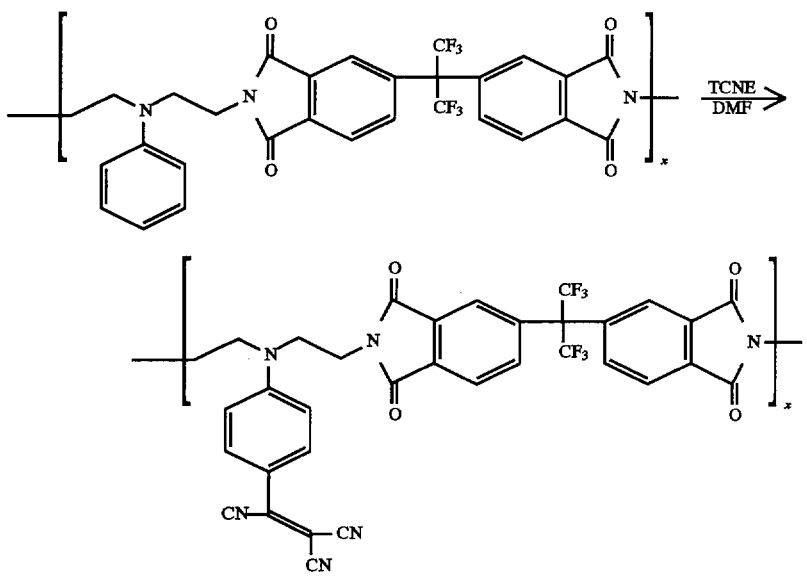

versatile family of compounds that can be readily varied to increase second order NLO properties.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. All such modifications are intended to be included within the scope of the following claims.

What is claimed is:

1. A method for preparing a polyamic acid having non-linear optical (NLO) or pre-NLO side chains, which method comprises:

mixing in a polar aprotic solvent a 1:1 ratio of bis-(aromatic dicarboxylic acid anhydrides) and aromatic diamines, wherein either or both of said bis-(aromatic dicarboxylic acid anhydrides) and said aromatic diamines comprise bis-(aromatic dicarboxylic acid anhydrides) and aromatic diamines having at least one NLO or pre-NLO side chain present in a ratio of between about 1:99 and about 75:25 to unsubstituted bis-(acid anhydrides) and aromatic diamines;

so that a polyamic acid having NLO or pre-NLO side chains is formed in said polar aprotic solvent by condensation of said bis-(acid anhydrides) with said aromatic diamines; and wherein said NLO or pre-NLO side chains have the structure represented by:

D-R-A wherein D, R and A form a delocalized resonance configuration in which R is a pi-conjugated non-centrosymmetric moiety comprising at least one heteroaromatic ring, or at least one fused ring system comprising a heteroaromatic ring, A is hydrogen or an electron withdrawing moiety and D is an electron donating moiety covalently linked to said bis-(aromatic dicarboxylic acid anhydride) or said aromatic diamine by nucleophilic substitution, and either D or A is only substituted on said heteroaromatic ring of R.

2. The method of claim 1, wherein R comprises from one to ten aromatic rings or fused ring systems.

3. The method of claim 1, wherein said heteroaromatic ring comprises a five-membered heteroaromatic ring.

4. The method of claim 3, wherein said five-membered heteroaromatic ring has the structure:

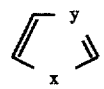

wherein Y is C or N and X is selected from the group consisting of O, S, Se, Te and N.

5. The method of claim 4, wherein all of said rings comprise said five-membered heteroaromatic ring, and all of said fused ring systems contain said five-membered heteroaromatic ring.

6. The method of claim 2, wherein R comprises two or more rings or fused ring systems linked together to form a delocalized resonance configuration.

7. The method of claim 6, wherein R comprises from two to four aromatic rings or fused ring systems.

8. The method of claim 6, wherein at least two adjacent rings or fused ring systems are linked together by a conjugated functional group comprising from one to three moieties independently selected from the group consisting of —N=N—, —CH=N—, —CH=N—N=CH—, —C≡C—, and (—CH=CH)$_j$—, wherein j is from one to three.

9. The method of claim 6, wherein at least two adjacent rings or fused ring systems are linked together by at least one non-conjugated linkage.

10. The method of claim 6, wherein said two or more rings or fused ring systems comprise at least two adjacent rings or fused ring systems directly covalently bonded together without forming a fused structure of said adjacent pair.

11. The method of claim 2, wherein R comprises one or more aromatic rings independently selected from the group consisting of pyrrole, furan, thiophene, imidazole, oxazole, thiazole, triazole, tetrazole, pyrazole, pyrimidine, purine, quinolines, carbazole, furazan, pyrazine, indole, isoindole, indazole, phenothiazine, benzotriazole, quinazoline, pteridine, azophenanthrenes, pyrones and chromones.

12. The method of claim 11, wherein said one or more aromatic rings are independently selected from the group consisting of pyrole, furan, thiophene, thiazole and oxazole.

13. The method of claim 2, wherein R comprises at least one fused ring system.

14. The method of claim 2, wherein R consists of a single fused ring system.

15. The method of claim 14, wherein said fused ring system comprises at least one five-membered heteroaromatic ring having the structure:

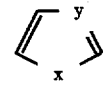

wherein Y is C or N and X is selected from the group consisting of O, S, Se, Te and N.

16. The method of claim 1, wherein A is hydrogen.

17. The method of claim 1, wherein said electron accepting moiety is selected from the group consisting of —NO$_2$, —CN, —CHO, —COR$_3$, —COOR$_3$, —PO(OR$_3$)$_3$, —SO$_2$R$_3$, —SO$_3$R$_3$, —PO(R$_3$)$_2$, dicyanovinylpyrones and —CX=CYZ, wherein X, Y and Z are independently selected from the group consisting of hydrogen, —CN, —NO$_2$, —COR$_3$, —COOR$_3$, —SO$_2$R$_3$, —PO(R$_3$)$_2$ and —PO(OR$_3$)$_2$, wherein R$_3$ is selected from the group consisting of alkyl moieties containing up to 15 carbon atoms.

18. The method of claim 17, wherein said electron accepting moiety comprises tricyanoethylene.

19. The method of claim 1, wherein said electron accepting moiety is selected from the group consisting of N,N-dialkylbarbituric acids, N,N-dialkylthiobarbituric acids, N,N-diarylbarbituric acids, N,N-diarylthiobarbituric acids, rhodamines, hydrantoins, oxazolines and ring moieties having the structure:

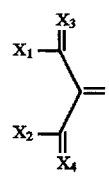

wherein X$_1$ and X$_2$ form a saturated or unsaturated five- to eight-member cyclic ring or two-ring system having five- to eight-member rings, and X$_3$ and X$_4$ are independently selected from the group consisting of O, S and $CI_1I_2$, wherein $I_1$ and $I_2$ of $X_3$ and $X_4$ are independently selected from the group consisting of —CN, —$NO_2$, —$COR_3$, —$COOR_3$, —$SO_2R_3$, —$PO(R_3)_2$ and —$PO(OR_3)R_2$, and $R_3$ is an alkyl group containing up to 15 carbon atoms.

20. The method of claim 19, wherein A comprises a moiety selected from the group consisting of 3-dicyanovinylindane-1-sulfone, 1,3-bissulfonylindane, indane-1,3-dione, 3-dicyanovinylindane-1-one and 1,3-bisdicyanovinylindane.

21. The method of claim 1, wherein said electron accepting moiety comprises a first electron accepting moiety and said NLO or pre-NLO side chain further includes a second electron accepting group attached to the same ring as said first electron accepting moiety, so that said delocalized resonance configuration is maintained.

22. The method of claim 1, wherein D is an electron donating moiety selected from the group consisting of —$NR_6R_7$—, —$OR_8$—, —$SR_8$—, —$TeR_8$—, —$SeR_8$—, —CH=$NR_9$—, —CH=N—$NR_6R_7$— and —CH=C[N($R_6R_7$)]$_2$—, wherein $R_6$ and $R_7$ are independently selected from the group consisting of hydrogen, alkyl groups containing up to 12 carbon atoms and groups derived from functionalized alkyl groups containing up to 12 carbon atoms, provided that at least one of $R_6$ or $R_7$ is a group derived from a functionalized alkyl group, or $R_6$ and $R_7$ together form a cyclic group containing up to 8 carbon atoms and substituted with a functionalized alkyl group containing up to 8 carbon atoms; $R_8$ is a group derived from a functionalized alkyl group containing up to 6 carbon atoms; and $R_9$ is a group derived from a functionalized alkyl group containing up to 10 carbon atoms; and said functionalized alkyl groups are functionalized with a nucleophilic substituent through which said electron donating moiety is covalently linked to said bis-(aromatic dicarboxylic acid anhydride).

23. The method of claim 22, wherein said alkyl group functionalized with a nucleophilic substituent is selected from the group consisting of alkoxy, aminoalkyl, alkylhalide, hydroxyalkyl, alkylsulfide, alkylisocyanate, alkylisothiocyanate, alkylthiol, alkylazide, alkylcarboxylic, alkylsulfonic, alkylalkene and alkylalkyne groups.

24. The method of claim 22, wherein $R_6$ and $R_7$ together form a cyclic group selected from the group consisting of pyrrolidine, piperidine, piperazine and morpholine groups.

25. The method of claim 1, wherein D comprises an electron donating moiety having the structure:

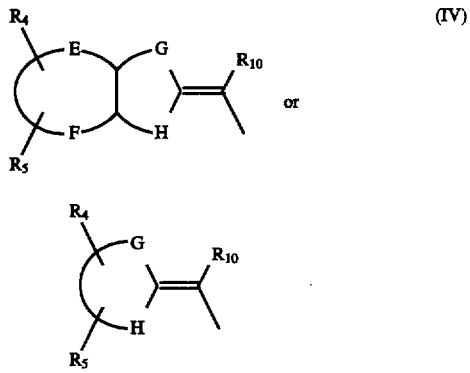

(IV)

wherein E, F, G and H are members of a saturated or unsaturated five- to eight-membered cyclic ring or two-ring system having five- to eight-membered rings that are electron donating in nature and are independently selected from the group consisting of —CH—, —$CH_2$—, O, N, S, Se, Te and —$NR_{11}$; and $R_4$, $R_5$, $R_{10}$ and $R_{11}$ are independently selected from the group consisting of hydrogen, alkyl groups containing up to 18 carbon atoms and groups derived from functionalized alkyl groups containing up to 18 carbon atoms, provided that at least one of $R_4$, $R_5$, $R_{10}$ and $R_{11}$ is a group derived from a functionalized alkyl group, and said functionalized alkyl groups are functionalized with a nucleophilic substituent through which said electron donating moiety is covalently linked to said bis-(aromatic dicarboxylic acid anhydride).

26. The method of claim 25, wherein D comprises an electron donating moiety selected from the group consisting of 1,3-dithiolium, 2-benzo-1,3-dithiolium and 2-ethylenedithio-1,3-dithiolium moieties.

27. The method of claim 1, wherein said electron donating moiety comprises a first electron donating moiety and said NLO or pre-NLO side chain further includes a second electron donating moiety attached to the same ring as said first electron donating moiety, so that said delocalized resonance configuration is maintained.

28. The method of claim 1, wherein said bis-(aromatic dicarboxylic acid anhydride) having at least one NLO or pre-NLO side chain in prepared by mixing in an aprotic solvent at a temperature between about −10° C. and about 25° C. two moles of an aromatic dicarboxylic acid anhydride substituted with a moiety capable of undergoing nucleophilic substitution with one mole of an NLO or pre-NLO compound having a structure represented by:

D-R-A so that a bis-(aromatic dicarboxylic acid anhydride) having an NLO or pre-NLO side chain is formed by nucleophilic substitution; wherein D, R and A form a delocalized resonance configuration in which R is a pi-conjugated non-centrosymmetric moiety, A is hydrogen or an electron withdrawing moiety and D is an electron donating moiety containing two nucleophilic substituents.

29. The method of claim 28, wherein D is an electron donating moiety selected from the group consisting of —$NR_6R_7$, —CH=$NR_6R_7$ and —CH=C[N($R_6R_7$)]$_2$, wherein $R_6$ and $R_7$ are independently selected from the group consisting of alkyl groups containing up to 12 carbon atoms and functionalized with a nucleophilic substituent or $R_6$ and $R_7$ together form a cyclic group containing up to 8 carbon atoms substituted with two alkyl groups containing up to 12 carbon atoms and functionalized with a nucleophilic substituent, provided that when D is —CH=C[N($R_6R_7$)]$_2$, up to two of the four $R_6$ and $R_7$ groups may be independently selected from the group consisting of hydrogen and alkyl groups containing up to 12 carbon atoms, or both N($R_6R_7$) groups may together form a cyclic group containing up to 8 carbon atoms substituted with one alkyl group containing up to 12 carbon atoms and functionalized with a nucleophilic substituent.

30. The method of claim 29, wherein said alkyl group functionalized with a nucleophilic substituent is selected from the group consisting of alkoxy, aminoalkyl, alkylhalide, hydroxyalkyl, alkylsulfide, alkylthiol, alkylazide, alkylcarboxylic, alkylsulfonic, alkylisocyanate, alkylisothiocyanate, alkylalkene and alkylalkyne groups.

31. The method of claim 29, wherein $R_6$ and $R_7$ together form a cyclic group selected from the group consisting of pyrrolidine, piperidine, piperazine and morpholine groups.

32. The method of claim 28, wherein D comprises an electron donating moiety having the structure:

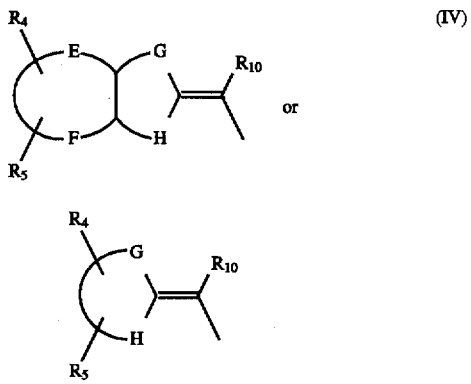

(IV)

wherein E, F, G and H are members of a saturated or unsaturated five- to eight-membered cyclic ring or two-ring system having five- to eight-membered rings that are electron donating in nature and are independently selected from the group consisting of —CH—, —CH$_2$—, O, N, S, Se, Te and —NR$_{11}$—; and R$_4$, R$_5$, R$_{10}$ and R$_{11}$ are independently selected from the group consisting of hydrogen, alkyl groups containing up to 18 carbon atoms and alkyl groups containing up to 18 carbon atoms functionalized with a nucleophilic substituent, provided that at least two of R$_4$, R$_5$, R$_{10}$ and R$_{11}$ comprise alkyl groups containing up to 18 carbon atoms functionalized with a nucleophilic substituent.

33. The method of claim 1, further comprising the step of refluxing said common solvent after said polyamic acid has been formed therein at a temperature at which said polyamic acid intramolecularly condenses to form a polyimide having NLO or pre-NLO side chains.

34. A polyamic acid having NLO or pre-NLO side chains, prepared by the method of claim 1.

35. A polyimide having NLO or pre-NLO side chains prepared by the method of claim 33.

36. The method of claim 1, wherein said aromatic diamine having at least one NLO or pre-NLO side chain is prepared by mixing in a polar solvent at a temperature between about 0° and about 50° C. two moles of an aromatic amine substituted with a moiety capable of undergoing nucleophilic substitution with one mole of an NLO or pre-NLO compound having a structure represented by:

D-R-A so that an aromatic diamine having an NLO or pre-NLO side chain is formed by nucleophilic substitution; wherein D, R and A form a delocalized resonance configuration in which R is a pi-conjugated non-centrosymmetric moiety, A is hydrogen or an electron withdrawing moiety and D is an electron donating moiety containing two nucleophilic substituents.

37. The method of claim 33, wherein D is an electron donating moiety selected from the group consisting of —NR$_6$R$_7$, —CH=NR$_6$R$_7$ and —CH=C[N(R$_6$R$_7$)]$_2$, wherein R$_6$ and R$_7$ are independently selected from the group consisting of alkyl groups containing up to 12 carbon atoms and functionalized with a nucleophilic substituent or R$_6$ and R$_7$ together form a cyclic group containing up to 8 carbon atoms and substituted with two alkyl groups containing up to 12 carbon atoms and functionalized with a nucleophilic substituent, provided that when D is —CH=C[N(R$_6$R$_7$)]$_2$, up to two of the four R$_6$ and R$_7$ groups may be independently selected from the group consisting of hydrogen and alkyl groups containing up to 12 carbon atoms, or both N(R$_6$R$_7$) groups may together form a cyclic group containing up to 8 carbon atoms and substituted with one alkyl group containing up to 12 carbon atoms and functionalized with a nucleophilic substituent.

38. The method of claim 37, wherein said alkyl group functionalized with a nucleophilic substituent is selected from the group consisting of alkoxy, aminoalkyl, alkylhalide, hydroxyalkyl, alkylsulfide, alkylthiol, alkylazide, alkylcarboxylic, alkylsulfonic, alkylisocyanate, alkylisothiocyanate, alkylalkene and alkylalkyne groups.

39. The method of claim 37, wherein R$_6$ and R$_7$ together form a cyclic group selected from the group consisting of pyrrolidine, piperidine, piperazine and morpholine groups.

40. The method of claim 36, wherein D comprises an electron donating moiety having the structure:

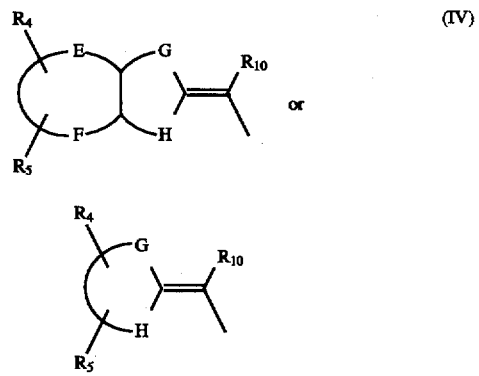

(IV)

wherein E, F, G and H are members of a saturated or unsaturated five- to eight-membered cyclic ring or two-ring system having five- to eight-membered rings that are electron donating in nature and are independently selected from the group consisting of —CH—, —CH$_2$—, O, N, S, Se, Te and —NR$_{11}$—; and R$_4$, R$_5$, R$_{10}$ and R$_{11}$ are independently selected from the group consisting of hydrogen, alkyl groups containing up to 18 carbon atoms and alkyl groups containing up to 18 carbon atoms functionalized with a nucleophilic substituent, provided that at least two of R$_4$, R$_5$, R$_{10}$ and R$_{11}$ comprise alkyl groups containing up to 18 carbon atoms functionalized with a nucleophilic substituent.

41. The method of claim 1, wherein said aromatic diamine having at least one NLO or pre-NLO side chain is prepared by mixing in a polar solvent at a temperature between about 0° and about 50° C. one mole of an aromatic amine substituted with a moiety capable of undergoing nucleophilic substitution with one mole of an NLO or pre-NLO compound having a structure represented by:

D-R-A so that an aromatic diamine having an NLO or pre-NLO side chain is formed by nucleophilic substitution; wherein D, R and A form a delocalized resonance configuration in which R is a pi-conjugated non-centrosymmetric moiety, A is hydrogen or an electron withdrawing moiety and D is an electron donating moiety containing two alkylamino groups of up to 12 carbon atoms each.

42. The method of claim 41, wherein D is an electron donating moiety selected from the group consisting of —$NR_6R_7$, —$CH=NR_6R_7$ and —$CH=C[N(R_6R_7)]_2$, wherein $R_6$ and $R_7$ are independently selected from the group consisting of alkylamino groups containing up to 12 carbon atoms, or $R_6$ and $R_7$ together form a cyclic group containing up to 8 carbon atoms and substituted with two alkylamino groups containing up to 12 carbon atoms, provided that when D is —$CH=C[N(R_6R_7)]_2$, up to two of the four $R_6$ and $R_7$ groups may be independently selected from the group consisting of hydrogen and alkyl groups containing up to 12 carbon atoms, or both $N(R_6R_7)$ groups may together form a cyclic group containing up to 8 carbon atoms substituted with one alkylamino group containing up to 12 carbon atoms.

43. The method of claim 42, wherein said alkyl group functionalized with a nucleophilic substituent is selected from the group consisting of alkoxy, aminoalkyl, alkylhalide, hydroxyalkyl, alkylsulfide, alkylthiol, alkylazide, alkylcarboxylic, alkylsulfonic, alkylisocyanate, alkylisothiocyanate, alkylalkene and alkylalkyne groups.

44. The method of claim 42, wherein $R_6$ and $R_7$ together form a cyclic group selected from the group consisting of pyrrolidine, piperidine, piperazine and morpholine groups.

45. The method of claim 41, wherein D comprises an electron donating moiety having the structure:

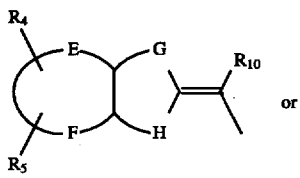

(IV)

or

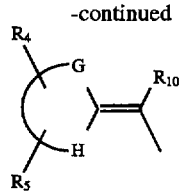

-continued wherein E, F, G and H are members of a saturated or unsaturated five- to eight-membered cyclic ring or two-ring system having five- to eight-membered rings, that are electron-donating in nature and are independently selected from the group consisting of —CH—, —$CH_2$—, O, N, S, Se, Te and —$NR_{11}$—; and $R_4$, $R_5$, $R_{10}$ and $R_{11}$ are independently selected from the group consisting of hydrogen, alkyl groups containing up to 18 carbon atoms and amino alkyl groups containing up to 18 carbon atoms, provided that at least two of $R_4$, $R_5$, $R_{10}$ and $R_{11}$ comprise amino alkyl groups containing up to 18 carbon atoms.

46. The method of claim 33, wherein A is hydrogen, so that said polyimide contains pre-NLO side chains, and said method further comprises the steps of:
  recovering said polyimide;
  dissolving in a basic solvent said recovered polyimide and a reagent capable of reacting with said pre-NLO side chains to attach covalently electron accepting moieties thereto; and
  heating said basic solvent so that said reagent reacts with said pre-NLO side chains whereby electron accepting moieties are covalently attached to said pre-NLO side chains.

47. A polyimide having NLO side chains prepared by the method of claim 46.

* * * * *

UNITED STATES PATENT AND TRADEMARK OFFICE
CERTIFICATE OF CORRECTION

PATENT NO. : 5,688,906      Page 1 of 2
DATED      : November 18, 1997
INVENTOR(S) : Jen et al.

It is certified that error appears in the above-identified patent and that said Letters Patent is hereby corrected as shown below:

On the title page, under the heaing "Related U.S. Application Data", on the fourth line of "[63]", "Nov. 24, 1995" should read --Nov. 24, 1993--.

Column 13, line 58, "NLO) or" should read --NLO or--

Column 14, line 66, "aidehyde" should read --aldehyde--.

Column 17, lines 40-53, in Example 3:

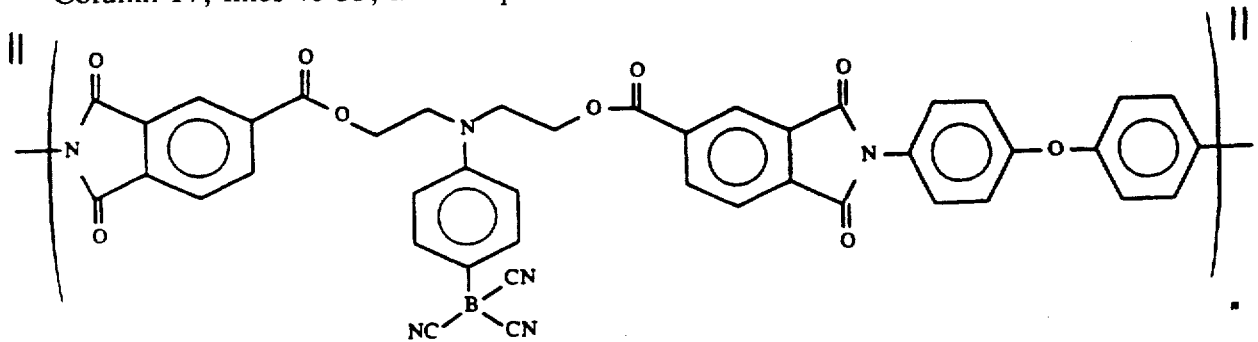

should read

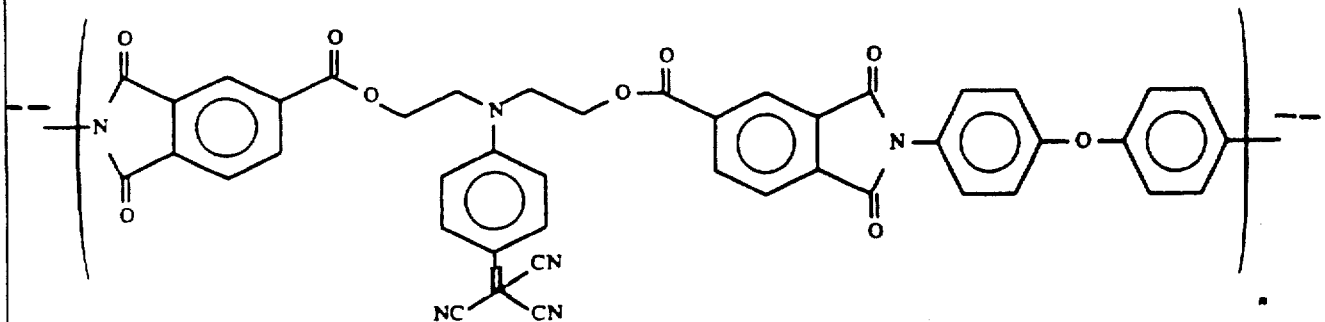

UNITED STATES PATENT AND TRADEMARK OFFICE
CERTIFICATE OF CORRECTION

PATENT NO. : 5,688,906

DATED : November 18, 1997

INVENTOR(S) : Jen et al.

It is certified that error appears in the above-identified patent and that said Letters Patent is hereby corrected as shown below:

Column 18 and Column 19, under "Example 4" should read:

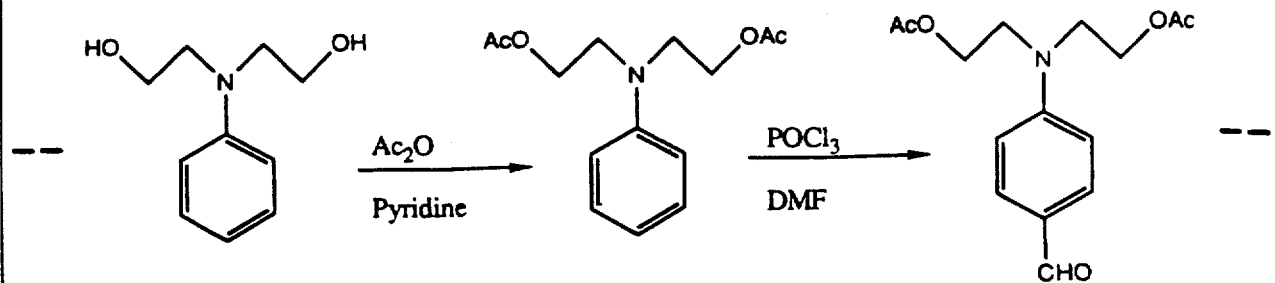

Column 29, line 59, first line of claim 37, "claim 33" should read --claim 36--.

Signed and Sealed this

Fourteenth Day of July, 1998

*Attest:*

BRUCE LEHMAN

*Attesting Officer*    *Commissioner of Patents and Trademarks*